US008041583B2

(12) United States Patent
Albro et al.

(10) Patent No.: US 8,041,583 B2
(45) Date of Patent: Oct. 18, 2011

(54) SYSTEM AND METHOD FOR ENHANCING ORGANIZATIONAL EFFICIENCIES TO DELIVER HEALTH CARE IN AN AMBULATORY HEALTH CARE SETTING

(76) Inventors: Thomas W. Albro, Seattle, WA (US); Jonathan B. Solomon, Seattle, WA (US)

( * ) Notice: Subject to any disclaimer, the term of this patent is extended or adjusted under 35 U.S.C. 154(b) by 430 days.

(21) Appl. No.: 12/123,433

(22) Filed: May 19, 2008

(65) Prior Publication Data

US 2009/0106051 A1    Apr. 23, 2009

Related U.S. Application Data

(63) Continuation-in-part of application No. 12/102,863, filed on Apr. 14, 2008.

(60) Provisional application No. 60/938,932, filed on May 18, 2007, provisional application No. 60/911,502, filed on Apr. 12, 2007.

(51) Int. Cl.
*G06Q 10/00* (2006.01)
(52) U.S. Cl. .................................. 705/3; 705/2; 707/608
(58) Field of Classification Search .................. 705/2–3; 707/608
See application file for complete search history.

(56) References Cited

U.S. PATENT DOCUMENTS

| 6,031,526 | A | 2/2000 | Shipp et al. | |
|---|---|---|---|---|
| 6,322,502 | B1 | 11/2001 | Schoenberg et al. | |
| 6,900,807 | B1 | 5/2005 | Liongosari et al. | |
| 2002/0194029 | A1* | 12/2002 | Guan et al. | 705/3 |
| 2003/0125987 | A1* | 7/2003 | Rucker | 705/3 |
| 2004/0128323 | A1 | 7/2004 | Walker et al. | |
| 2004/0143689 | A1 | 7/2004 | Leavitt | |
| 2005/0021369 | A1* | 1/2005 | Cohen et al. | 705/2 |
| 2005/0108052 | A1* | 5/2005 | Omaboe | 705/2 |
| 2005/0256746 | A1 | 11/2005 | Zaleski et al. | |
| 2006/0041450 | A1* | 2/2006 | Dugan | 705/2 |
| 2007/0038474 | A1* | 2/2007 | Halsted | 705/2 |
| 2007/0136095 | A1* | 6/2007 | Weinstein | 705/2 |
| 2008/0312959 | A1* | 12/2008 | Rose et al. | 705/2 |

* cited by examiner

*Primary Examiner* — Gerald J. O'Conner
*Assistant Examiner* — Sind Phongsvirajati
(74) *Attorney, Agent, or Firm* — Richard T. Black

(57) ABSTRACT

The invention is a system and method for managing patient care workflow, staff and resource allocation in real time in an ambulatory health care (clinic) setting providing the clinic with improved operating efficiencies. The system can stand alone or integrate seamlessly with enabling Electronic Health Record (EHR) applications by presenting the most relevant EHR view and form to the user at appropriate times in the workflow. Embodiments of the invention provide users with enhanced clinical practice functionality, efficiency and effectiveness.

20 Claims, 13 Drawing Sheets

| Provider | Pending Arrival | Reception | With MA | Exam | | Procedure |
|---|---|---|---|---|---|---|
| Miranda Bailey, MD 28 patients 14 complete | Wilson Est. 73 | Taft Device 60 | Hoover New Pt. 5 | Overman Solomon Est. Consult 30 18 | Morrill Recheck 206 | Hayes Est. 207 | Bassett Est. 208 | Fillmore Stress Echo4 |
| Preston Burke, MD 12 patients 8 complete | Wilson Est. 37 | Cleveland Est. 35 | Latimer Consult 30 | Alhro Est. 15 | Johnson Est. 205 | Bassett Est. 204 | |
| Frank Burns, ARNP 6 patients 3 complete | Arthur Post Op. 0 | | | | Nixon New Pt. 203 | | |
| Ben Casey, MD 21 patients 10 complete | Garfield Hayes Est. New Pt. 10 8 | | Roosevelt Device Chk. 5 | | | | Grant Stress Est. Echo3 |
| Beverly Crusher, MD 28 patients 14 complete | Grant Est. 0 | | | | | | Van Dyke Est. 102 |
| Mark Doctor, MD 25 patients 11 complete | Sumner Taylor Consult New Pt. 60 40 | | Hoover Lincoln Est. Est. 30 25 | Roosevelt Consult 15 | Grant Est. 102 | Polk Est. 209 | | Mangum Abn. Echo Echo2 |
| John Dolittle, ARNP 14 patients 7 complete | Buchanan Pierce Est. New Pt. 5 5 | | Washington Post Op. 15 | | | Lincoln Post Op. 210 | Jones Stress Echo1 | |
| H. Frankenstein, MD 32 patients 4 complete | Tyler Est. 5 | | Jefferson Stress Test 5 | | Laurens New Pt. 103 | Adams Est. 106 | |
| Meredith Grey, MD 22 patients 13 complete | Harrison Van Bur New Pt. Est. 14 12 | | Madison Henry Est. Est. 15 5 | | Carter Est. 108 | Adams Est. 105 | |
| Henry Jeckyll, MD 28 patients 11 complete | Jackson Post Op. 6 | | Coolidge New Pt. 5 | | Carter Est. 109 | Calhoun Est. 107 | | Arthur Doppler Study1 |
| James Kildare, MD 15 patients 6 complete | | | | | | Wilson New Pt. 110 | |
| Leonard McCoy, MD 12 patients 4 complete | Monroe Adams Est. Est. 0 0 | | Harding Est./Stress | | Taft Est. 113 | Harrison Est. 112 | | Reagan Bubble Study2 |

SYSTEM AND METHOD FOR ENHANCING ORGANIZATIONAL EFFICIENCIES TO DELIVER HEALTH CARE IN AN AMBULATORY HEALTH CARE SETTING

PRIORITY CLAIM

This application claims priority to U.S. Patent Application Ser. No. 60/938,932 filed May 18, 2007. This application is also a continuation-in-part of U.S. patent application Ser. No. 12/102,863 filed Apr. 14, 2008, which application claims priority to earlier filed U.S. Provisional Patent Application Ser. No. 60/911,502 filed Apr. 12, 2007. All of the foregoing applications are hereby incorporated by reference in their entirety as if fully set forth herein.

COPYRIGHT NOTICE

This disclosure is protected under United States and International Copyright Laws. © 2008 PROSCRIBE, INC. All Rights Reserved. A portion of the disclosure of this patent document contains material which is subject to copyright protection. The copyright owner has no objection to the facsimile reproduction by anyone of the patent document or the patent disclosure after formal publication by the U.S. Patent Office, as it appears in the U.S. Patent and Trademark Office patent file or records, but otherwise reserves all copyright rights whatsoever.

FIELD OF THE INVENTION

This invention relates generally to systems and methods for improving organizational efficiencies of delivering health care in an ambulatory health care setting by providing comprehensive, intuitive, patient focused, and user driven workflow tools.

BACKGROUND OF THE INVENTION

Ambulatory health care settings (those that see patients in an out-patient environment verses in an in-patient hospital environment) are ubiquitous in every developed society. In the United States, almost every ambulatory health care setting (clinic) has multiple health care providers who are assisted by a larger number of staff in providing care and administrating the clinic.

Providing health care is resource intensive endeavor. These resources include physicians, medical technicians, medical assistants, nurses, other clinical and administrative staff, extensive facilities (e.g., waiting rooms, exam rooms, offices), and various types of equipment (everything from simple scales to very expensive and complicated diagnostic equipment).

Patient encounters typically require the successive involvement of many staff members and the use of several aspects of the facility and types of equipment. Each person involved in this chain of care has a specific role and uses various resources. For example—when a patient arrives at the clinic they "check-in" with the receptionist and wait in the waiting room; the patient is then escorted by a medical assistant to an exam room where the assistant gathers information and leaves the patient; subsequently the patient is seen by a physician or other provider; after the exam the patient then "checks-out" with a staff person before leaving the clinic. When tests, labs, or other studies are necessary even more people and resources are involved.

In the illustration above, the receptionist typically uses a Practice Management System to register the patient, often prepares portions of the medical record for clinical staff (particularly where paper health records are used), and alerts the clinical staff of the patient's presence; the medical assistant typically assigns the exam room, gathers patient health information for the medical record, prepares the patient for the provider, and alerts the provider of the patient's presence and updated health status; the provider examines the patient, records health information in the health record, orders treatment or study, and communicates the patient status to the medical assistant; and the "check-out" person typically records the visit as complete in the Practice Management System and coordinates subsequent patient visits and provider ordered treatment or study. So in this illustration the following clinical elements were involved: receptionist, medical assistant, provider, "check-out" staff, practice management system, medical record, waiting room, exam room, "check-out" counter, and whatever resources were required to administer the provider-ordered treatment or study.

The providing of care, by its very nature, is private. Patients are examined in private rooms and usually by only one provider or staff person at a time. This means that when a provider or other clinic member is in with a patient they are not available to their co-workers. This makes the coordinating of care efforts and resources difficult, time consuming, and prone to problems.

Systems and methods for coordinating these resources are known in the art and vary significantly in their approach, attributes, and common use. These include what are commonly referred to as Practice Management Systems, Electronic Health (or Medical) Records, other clinical workflow tools, and all manner of manual systems.

While such systems offer some benefits they generally fail to assist the clinic in attaining better resource utilization, higher efficiencies, and greater operational effectiveness. Tools provided are rarely tailored to what the specific clinic member needs for their role and that specific patient, nor do they ease the 'hand off' of patient care from one clinic member to the next.

Most systems focus on specific elements of the patient or encounter (e.g. as appointment time, visit type, chief complaint, payer, provider, health information, and the like) and do not help the clinic staff recognize the patient as a person. Patients therefore are often not recognized by the clinic staff attending to them, even though in many cases they are repeat visitors. This generally depersonalizes the encounter for both clinic member and patient alike, reducing the quality of the experience for all.

Administrators responsible for managing clinical staff and resources are generally hamstrung in their efforts to manage clinical staff and resources by the absence or unavailability of information. Most managers have precious little information regarding efficiencies, utilization, and effectiveness of the clinic overall and individual elements specifically.

The status of all patients in the clinic (e.g. who's currently attending them, where they are physically, how long they have been waiting, how long they are likely to wait) is impossible or difficult to monitor and track. Consequently, management is often in a reactive mode and responding to problems that could have been avoided if better information had been available.

Digital (electronic) documentation systems in the health care environment are well known in the art. Such systems are commonly called Electronic Health Records (EHR) or Electronic Medical Records (EMR). While EHR systems have the promise to improve both the quality and the efficiency of provided health care, current Electronic Health Record systems are generally cumbersome to use and offer little workflow assistance to clinic members.

Despite the recognition that EHR systems are in many ways compelling, their use is still met with a certain degree of opposition, skepticism, and limited success. It is apparent that until providers are offered EHR systems that are easy to use and empower their ability to care for patients, such resistance will persist.

One barrier to the adoption of an EHR system is the user-friendliness, i.e. "intelligence" of the interface. Current EHR systems frequently error on the side of over-inclusion; seeking to make input screens and data displays generic across medical specialties and clinical roles. Additionally, the EHR system interface generally requires users to re-enter information that is already known or to navigate through multiple-unrelated screens before they arrive at the interface that requires the clinic member's attention. As a result, most EHR system interfaces seem to present all of the patient information to every user all of the time, i.e. they don't intelligently present the information by presenting only the most pertinent information for the specific user. The distinct disadvantage with this approach is that productive time is lost inputting unnecessary information or navigating through the screens in the EHR application. Moreover, because the views are complicated and data-dense they are difficult to read; often obscuring the important and pertinent information. Chaotic and illogical formats not only present irrelevant, private, personal health information to more users than necessary, they also increase the opportunity for error.

Another barrier to the adoption of an EHR system is the inability to actually manage the provision of health care efficiently because of the inherent clinical (that is, health data) bias of most Electronic Health Records. For example, how long a patient visit was, how long a procedure took, how long a patient was waiting in the waiting room before examination, and the like, are completely lost variables in the current EHR scheme. In the current dichotomy, the procedural aspects of providing care are viewed as different from the actual care that was provided. The uncoupled nature of the medical workflow with the actual clinical work-product makes consistent work management practically impossible. The disadvantage of prior EHR systems is that the opportunity to integrate medical workflow with the actual clinical work-product in the EHR is completely lost.

Thus there is a need in the art for a comprehensive clinical workflow application that can work as a stand alone application or integrate with an Electronic Health Record system to manage medical office workflow in a user-friendly and easily adoptable format. Such a system would provide electronic storage, retrieval, analysis, and transmittal of information and have the advantage, amongst other things, of completely integrating the clinical workflow environment, thereby reducing the duplication of effort, the number of systems and personnel necessary to do multiple tasks, and increasing efficiency and cost-effectiveness.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee. The particular and alternative embodiments of the present invention are described in detail below with reference to the following drawings:

FIG. 6 depicts another exemplary embodiment of the invention and the operation of capturing a patient image;

FIG. 7 depicts another exemplary embodiment of the invention and the operation of capturing a patient image;

FIG. 12 depicts an exemplary embodiment of an interface for the invention showing the patient status and flow through the clinic;

DETAILED DESCRIPTION OF THE PREFERRED EMBODIMENT

Figure 1:
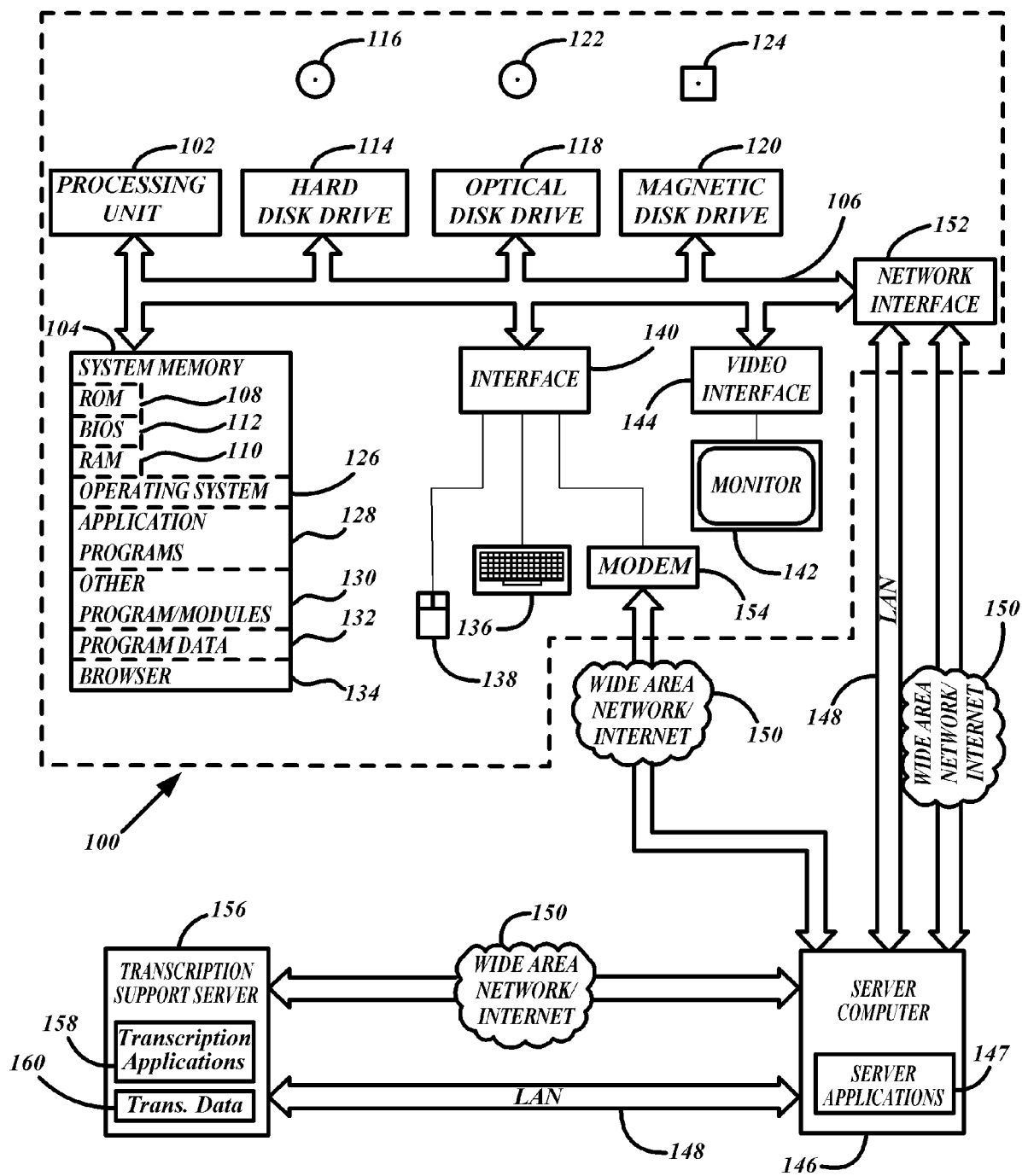
FIG. 1 depicts a block diagram of a computer system interacting with a server and an Electronic Health Record (EHR) server.

A system and method that enhances clinical efficiency in the delivery of health care by coordinating the efforts of all clinic members, allocating clinical resources, providing accurate information to clinic management, and calling specific forms at the appropriate time in the EHR is disclosed.

One embodiment of the present invention provides a system and method capturing a patient image and associating that image with a patient in an application database and automatically recording the patient as present in a scheduling system. For example, a scheduling system can be EHR database driven. This embodiment also automatically populates and prints paper forms if necessary (e.g., printed forms may be standard and/or customized medical data forms).

Another embodiment of the present invention provides a system and method for automatically centering, cropping, and receiving a patient image so the recorded patient image is of a uniform dimension and standard composition.

Another embodiment of the present invention provides a system and method of updating patient demographic and insurance information, for example, the information can be maintained in an EHR database.

Another embodiment of the present invention provides a system and method for displaying clinical and patient care status information in an interface customized to a user according to the user's clinical role and whereby the user is able to recognize a patient at the outset of their interaction with him or her.

Another embodiment of the present invention provides a system and method of immediately and automatically notifying an appropriate staff member of a patient's status and location (e.g., checked in and waiting in reception, ready for provider in Exam Room 3).

Another embodiment of the present invention provides a system and method for viewing real-time status and location of all patients in a clinic at a particular time.

Another embodiment of the present invention provides a system and method for estimating and viewing in real-time anticipated wait times for all patients scheduled for the day based on historical data and the actual clinical schedule performance for the day at that time.

Another embodiment of the present invention provides a system and method that enables authorized users to modify a clinic schedule directly in a screen presenting real-time status.

Another embodiment of the present invention provides a system and method that enables a user to access a patient's EHR information by double clicking the patient image.

Another embodiment of the present invention provides a system and method that enables a user to view all aspects of a clinic schedule (e.g., patients according to scheduled appointment, appointment type, status, physician) in an image-rich environment and in a view tailored to the user's clinical role.

Another embodiment of the present invention provides a system and method for allocating and denoting available clinical resources, for example, in one embodiment, exam rooms and equipment.

Another embodiment of the present invention provides a system and method that enables providers, medical technicians, and medical assistants to view in one screen a status and location of all patients under their care and present in a clinic and their schedule for any day, allowing users to best allocate and prioritize their time.

Another embodiment of the present invention provides a system and method that enables a user (for example, a provider, a medical technician, and a medical assistant) to view, in one screen, all patients under their care that require action. This embodiment also empowers the user to manage their time and prioritize efforts based on patient status, location, and urgency of a request.

Another embodiment of the present invention provides a system and method that enables a user to process and respond to requests, results, and other information (e.g. refilling prescriptions, reviewing lab results) pertaining to patients under their care while also managing their daily in-clinic patient flow. In one embodiment of the invention, an EHR database can be used (where EHR used and integration with this invention enabled).

Another embodiment of the present invention provides a system and method that works together as described in our co-pending U.S. patent application Ser. No. 12/102,863 filed Apr. 14, 2008 and enables a user, such as a provider, to review transcription, by, for example, listening to their corresponding dictation, and approving it thereby adding it to the permanent patient health record, and to do so while also managing their daily in-clinic patient flow.

Another embodiment of the present invention provides a system and method that presents real-time and historical clinical patient flow data, which can be, but is not limited to, data, such as average wait times, number of patients in the clinic, total patient time in the clinic, and other performance metrics.

Referring now to the figures, FIG. 1 describes an aspect of the workflow application and provides a general description of a computing environment that may be used to implement various aspects of the present invention. For purposes of brevity and clarity, embodiments of the invention may be described in the general context of computer-executable instructions, such as program application modules, objects, applications, models, or macros being executed by a computer, which may include but is not limited to personal computer systems, hand-held devices, multiprocessor systems, microprocessor-based or programmable consumer electronics, network PCs, mini computers, mainframe computers, and other equivalent computing and processing sub-systems and systems. Aspects of the invention may be practiced in distributed computing environments where tasks or modules are performed by remote processing devices linked through a communications network. Various program modules, data stores, repositories, models, objects, and their equivalents may be located in both local and remote memory storage devices.

By way of example, a conventional workstation computer, referred to in FIG. 1 herein as a computer 100, includes a processing unit 102, a system memory 104, and a system bus 106 that couples various system components including the system memory to the processing unit. The computer 100 will at times be referred to in the singular herein, but this is not intended to limit the application of the invention to a single computer since, in typical embodiments, there will be more than one computer or other device involved. The processing unit 102 may be any logic processing unit, such as one or more central processing units (CPUs), digital signal processors (DSPs), application-specific integrated circuits (ASICs), and the like. Unless described otherwise, the construction and operation of the various blocks shown in FIG. 1 are of conventional design. As a result, such blocks need not be described in further detail herein, as they will be understood by those skilled in the relevant art.

The system bus 106 can employ any known bus structures or architectures, including a memory bus with memory controller, a peripheral bus, and a local bus. The system memory 104 includes read-only memory ("ROM") 108 and random access memory ("RAM") 110. A basic input/output system ("BIOS") 112, which can form part of the ROM 108, contains basic routines that help transfer information between elements within the computer 100, such as during start-up.

The computer 100 also includes a hard disk drive 114 for reading from and writing to a hard disk 116, and an optical disk drive 118 and a magnetic disk drive 120 for reading from and writing to removable optical disks 122. The optical disk 122 can be a CDROM. The hard disk drive 114, optical disk drive 118, and magnetic disk drive 120 communicate with the processing unit 102 via the bus 106. The hard disk drive 114, optical disk drive 118, and magnetic disk drive 120 may include interfaces or controllers (not shown) coupled between such drives and the bus 106, as is known by those skilled in the relevant art. The drives 114, 118, 120, and their associated computer-readable media, provide nonvolatile storage of computer readable instructions, data structures, program modules, and other data for the computer 100. Although the depicted computer 100 employs hard disk 116 and optical disk 122, those skilled in the relevant art will appreciate that other types of computer-readable media that can store data accessible by a computer may be employed, such as magnetic cassettes, flash memory cards, digital video disks ("DVD"), USB memory sticks, and the like.

Program modules can be stored in the system memory 104, such as an operating system 126, one or more application programs 128, other programs or modules 130 and program data 132. Although the depicted embodiment shows the computer 100 as a personal computer, in other embodiments, the computer is some other computer-related device such as a personal data assistant (PDA), a cell phone, or other mobile device.

The operating system 126 may be stored in the system memory 104, as shown, while application programs 128, other programs/modules 130, program data 132, and browser 134 can be stored on the hard disk 116 of the hard disk drive 114 and/or the optical disk 122 of the optical disk drive 118. A user can enter commands and information into the computer 100 through input devices such as a keyboard 136 and a pointing device such as a mouse 138.

Certain deployments of a workflow application, such as a reception interface (FIG. 5), require a video camera 124. Other input devices can include, for example, a microphone, joystick, game pad, scanner, and the like. These and other input devices are connected to the processing unit 102 through an interface 140 such as a serial port interface that couples to the bus 106, although other interfaces such as a parallel port, a game port, a wireless interface, or a universal serial bus ("USB") can be used. A monitor 142 or other display device is coupled to the bus 106 via a video interface 144, such as a video adapter. The computer 100 can include other output devices, such as, for example, speakers, printers, and the like.

The computer 100 can operate in a networked environment using logical connections to one or more remote computers, such as a server computer 146. The server computer 146 is a server hosting the workflow application and a database. The server computer 146 can be connected to one or more of the computers 100 under any known method of permitting computers to communicate, such as through a local area network ("LAN") 148, or a wide area network ("WAN") or the Internet 150. Such networking environments are well known in wired and wireless enterprise-wide computer networks, intranets, extranets, and the Internet. Other embodiments include other types of communication networks, including telecommunications networks, cellular networks, paging networks, and other mobile networks. The server computer 146 is configurable to run server applications 147, preferably including the EHR database server application.

When used in a LAN networking environment, the computer 100 is connected to the LAN 148 through an adapter or network interface 152 (communicatively linked to the bus 106). When used in a WAN networking environment, the computer 100 often includes a modem 154 or other device, such as the network interface 152, for establishing communications over the WAN/Internet 150. The modem 154 may be communicatively linked between the interface 140 and the WAN/Internet 150. In a networked environment, program modules, application programs, or data, or portions thereof, can be stored in the server computer 146. In the depicted embodiment, the computer 100 is communicatively linked to the server computer 146 through the LAN 148 or the WAN/Internet 150 with TCP/IP middle layer network protocols; however, other similar network protocol layers are used in other embodiments. Those skilled in the relevant art will readily recognize that the network connections are some examples of establishing communication links between computers, and other links may be used, including, but not limited to, wireless links.

The Workflow Application and Database server computer 146 is further communicatively linked to an Electronic Health Record (EHR) server 156 typically through the LAN 148 or the WAN/Internet 150 or other networking configuration such as a direct asynchronous connection (not shown). Other embodiments may support the Workflow Application and Database server computer 146 and the EHR support system 156 on one computer system by operating all server applications, EHR applications and databases on the one computer system. The EHR server system 156 is configurable to run host applications 158, such as in system memory, and store host data, such as EHR 160 related data.

Figure 2:
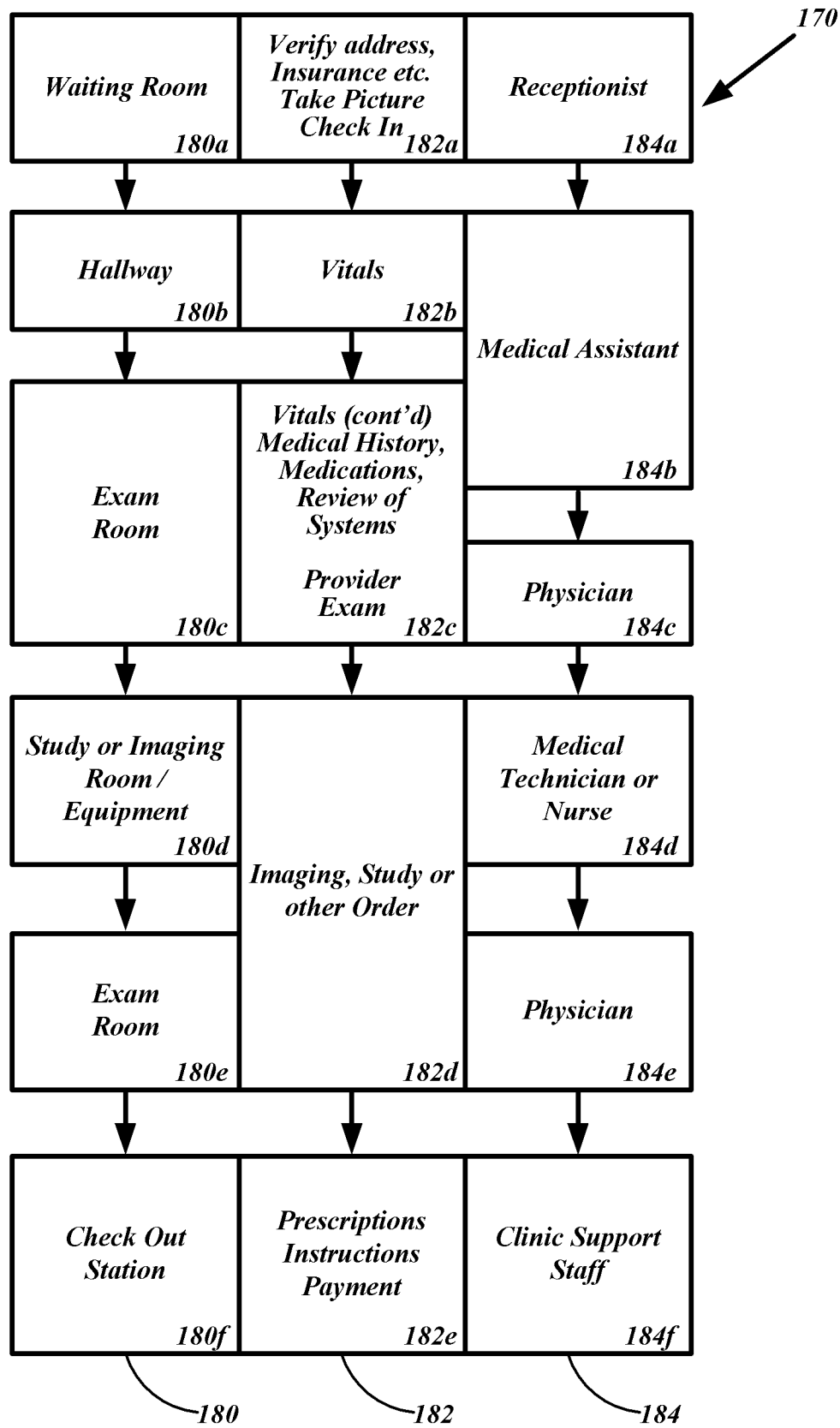
FIG. 2 depicts a flow chart of typical patient visit workflow.

FIG. 2 illustrates an exemplary patient flow 170 in an ambulatory healthcare setting. The left-most column 180 indicates a clinic resource or location where a function takes place (e.g. 180a-180f). The middle column 182 indicates clinical tasks during a patient encounter (e.g. 182a-182e), in an exemplary occurring order. The right-most column 184 indicates a user role and interface associated with a clinical task. Examples of user roles can include, but are not limited to those illustrated in 184a-184f.

Figure 3:
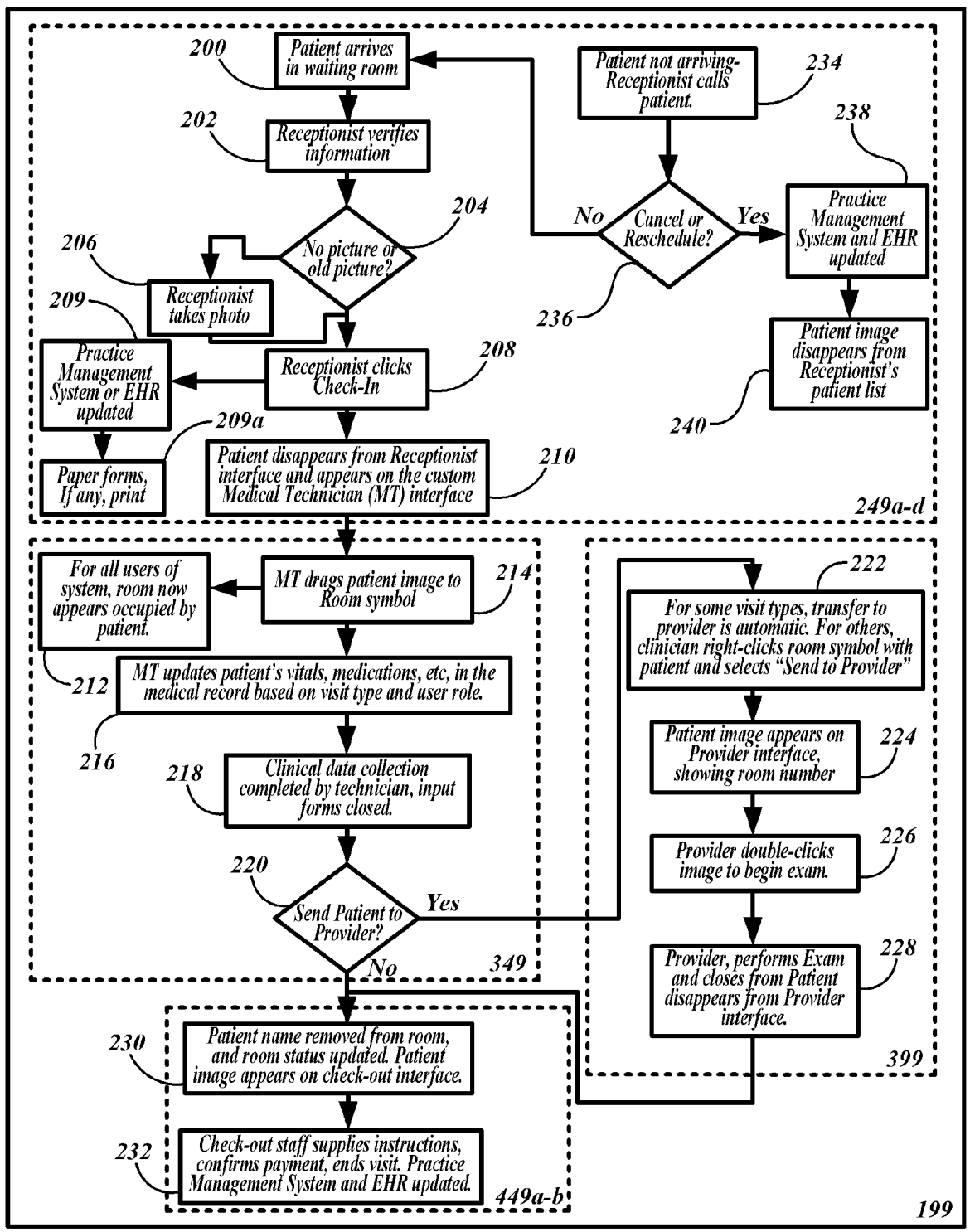
FIG. 3 depicts a flow chart of one exemplary embodiment of the system.

FIG. 3 is a flowchart illustrating an embodiment for a workflow application system 199 managing a patient encounter, improving clinical efficiency, coordinating staff, allocating clinical resources, and calling specific forms at an appropriate time in an EHR, if, for example, in an EHR environment wherein the EHR has been integrated (if EHR is present and integration possible).

In FIG. 3, a workflow application system 199 is illustrated. As illustrated in the Workflow Application System 199, includes sub-components "Receptionist" interface 249a-d, "Medical Assistant (MA)/Technologist (MT)" interface 349 and a "Provider" interface 399 and the "Management and Administrative" interface 449a-b.

Figure 4:
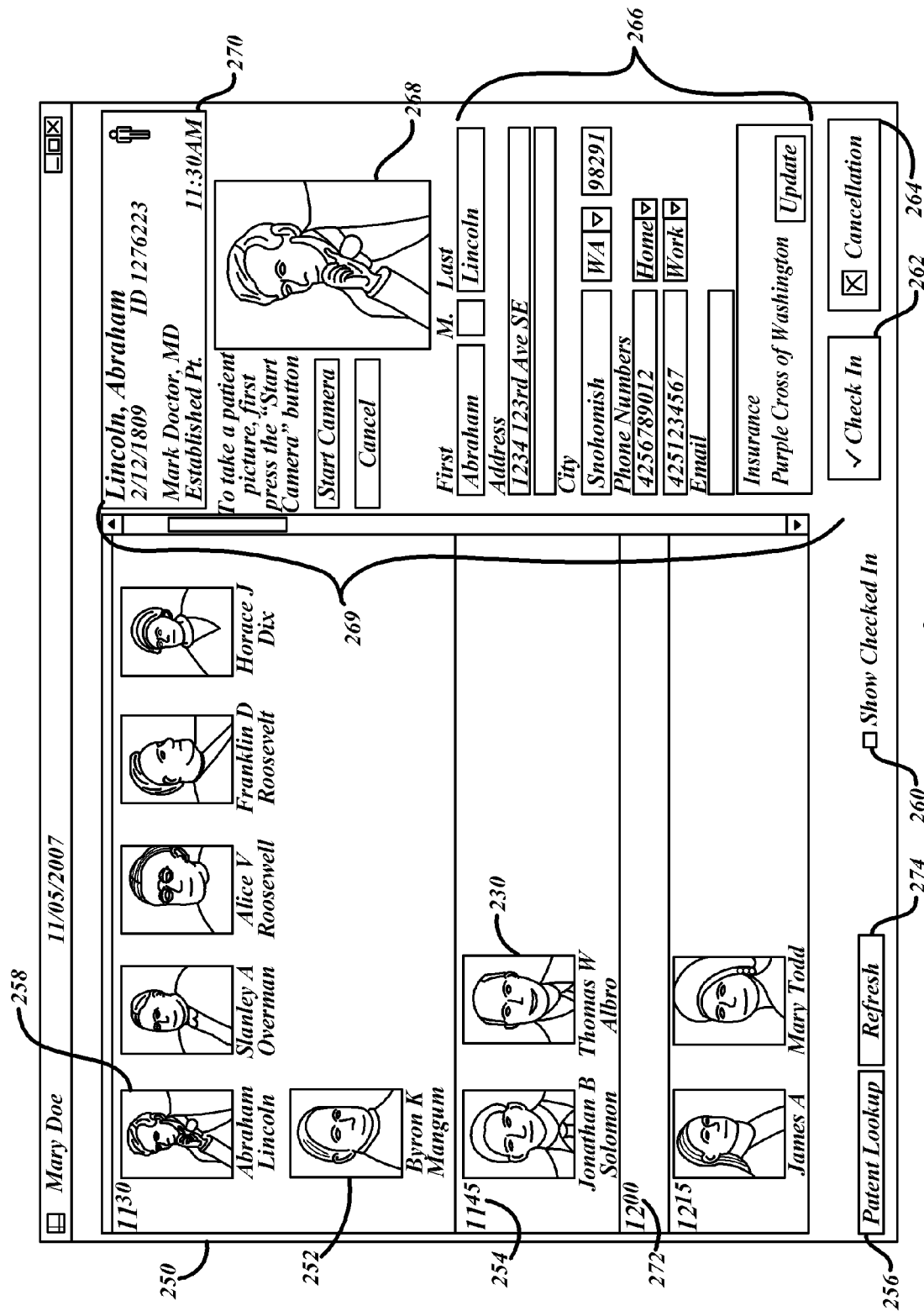
FIG. 4 depicts an exemplary embodiment of an interface for the invention and customized for a receptionist.

First, at Block 200, a patient arrives in a clinic and proceeds to a reception desk. At Block 202 the Receptionist confirms a patient appointment and provider availability and verifies patient demographic and insurance information (as shown in FIG. 4 266).

If there is no patient image or the image is out of date at decision block 204, the receptionist captures a new image (picture) at block 206. The receptionist can then check-in the patient at block 208, enter the data in the Practice Management System and/or EHR is automatically updated at Block 209, and paper forms (e.g. printed forms may be standard and/or customized medical data forms), if any, can be printed automatically 209a.

Figure 8:
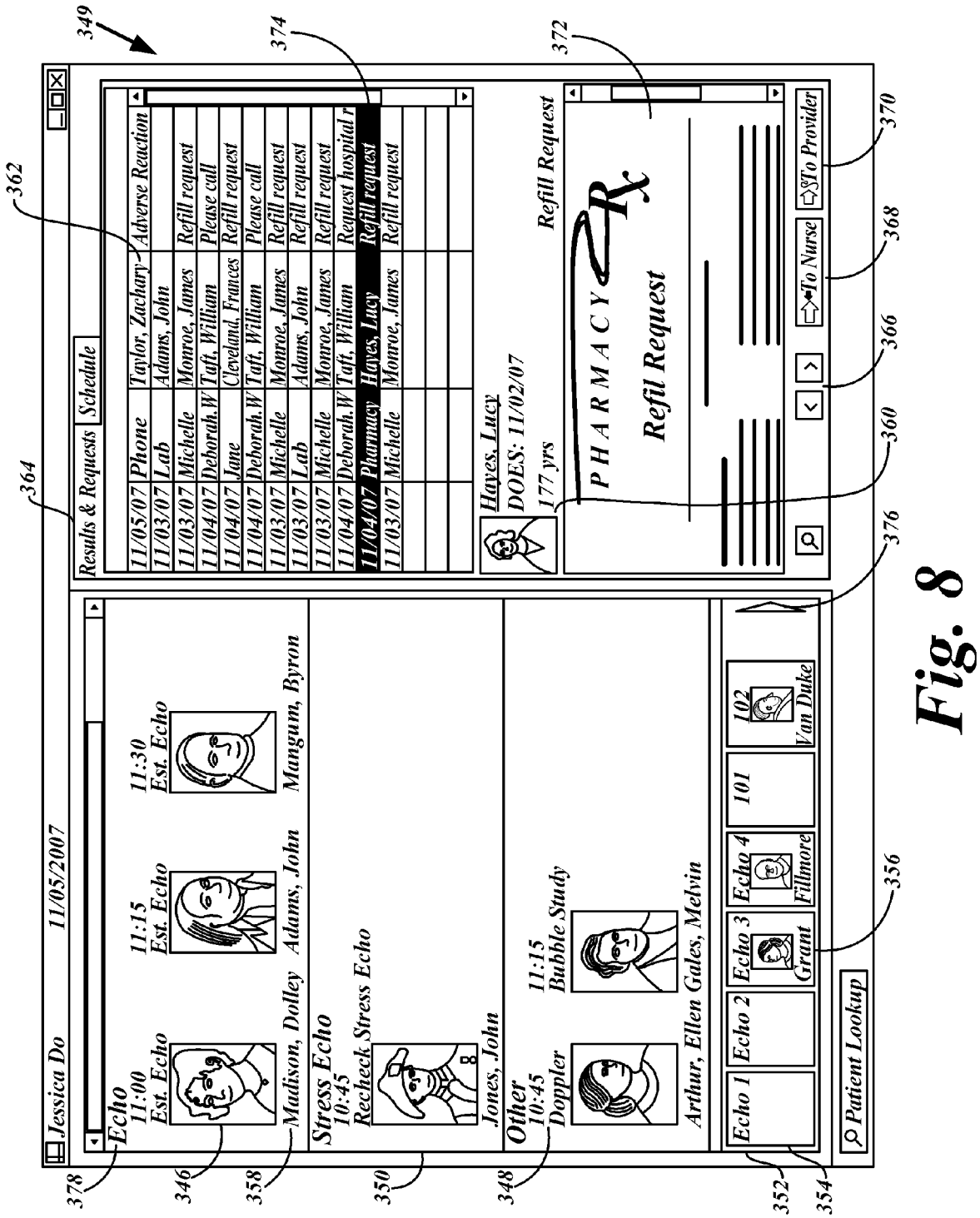
FIG. 8 depicts an exemplary embodiment of an interface for the invention customized for a Medical Assistant or Medical Technician.

At Block 210, the patient status can be changed as a result of the completion of the check-in process at Block 208, and is updated in the patient workflow database, thereby causing the patient image to disappear from the "Receptionist" interface 249a-d and automatically appear on the "Medical Technician (MT)" interface (see also FIG. 8 349). For example, a patient's image 268 as is shown in FIG. 4, in this example, disappears from the "Receptionist" interface 249a and appears in "Medical Assistant (MA)/Technologist (MT)" interface 349 (as shown in FIG. 8).

The presence of the patient image alerts the MT that the patient is in the waiting room, assigned to the MT and ready to be seen. The MT uses the patient image to identify the patient in the waiting area and begins the MT patient encounter by selecting and dragging the patient image to an available exam room at block 214. By doing so, room status in an application database is changed, thereby indicating to all system users that the room is occupied by the selected patient at block 212.

At an "MA/MT" interface (see for example FIG. 8 349), the MA/MT gathers and records health information from the patient at block 216 and when complete, closes any associated EHR forms at block 218, thereby changing the patient status in the application database. Referring again to FIG. 1, the Workflow Application 199 of FIG. 3 can overlays and integrate with commonly used Practice Management Systems and/or EHRs.

Turning back to FIG. 3, Block 220 represents an optional conditional branch in the workflow. For example, in one embodiment, the patient image (as appears in FIG. 4 258 and 268) can automatically appear on an interface of a clinical staff person responsible for continuing the next aspect of the patient encounter at block 224. Optionally, means are provided at block 222, to enable the clinical staff person caring for the patient to modify the patient workflow by forwarding the patient directly to Check-Out at block 230 versus being seen by a provider.

Figure 10:
FIG. 10 depicts an exemplary embodiment of a Patient Chart in EHR.
Figure 11:
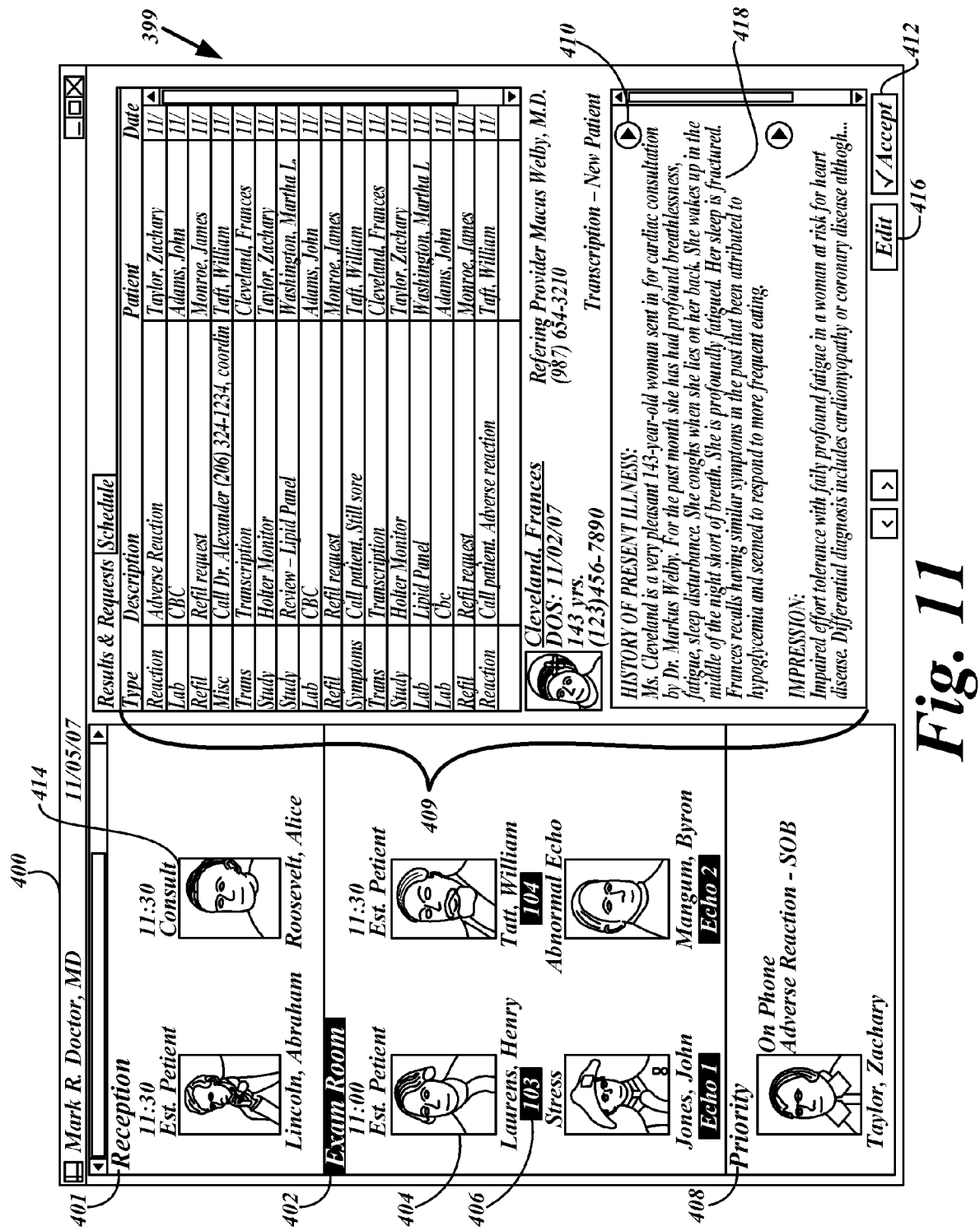
FIG. 11 depicts an exemplary embodiment of an interface for the invention customized for a Provider (physician, nurse practitioner, etc.)

When the patient is directed to a provider, automatically or otherwise, the provider double-clicks the patient image at a block 226 (as shown in FIG. 11) to continue the encounter and begin the provider-patient exam. In an EHR environment, for example, this will automatically call and present to the provider the most appropriate form for documenting the patient encounter (e.g., printed forms may be standard and/or customized medical data forms). For example, the provider may be presented with a chart view of a medication sheet as shown in FIG. 10.

At the conclusion of the provider-exam, the provider closes the form, automatically changing the patient status in the application database, causing the patient image to disappear from the provider interface at block 228 (see also FIG. 11) and automatically appear on the "Checkout" interface at block 230.

At Block 232, at a "Checkout" interface, the check-out staff is alerted that the patient is ready to conclude the visit. Tailored instructions based on the encounter are displayed and queued for printing. When the patient appears at a Checkout desk, a "Checkout" staff person identifies the patient from their image, confirms their identity and proceeds with checkout. At this point the Practice Management System and/or EHR are automatically updated (e.g., visit status, patient information provided and the like).

In the event that a scheduled appointment needs to be altered at block 236 (e.g. due to patient cancellation, no-show at block 234, clinical need to reschedule, and the like), the Receptionist selects the patient in the "Receptionist" interface at block 249a-d and clicks "Cancellation" button (see FIG. 4, 264). This action automatically changes the patient status in the application database, updates the Practice Management System and/or EHR 238 and removes the patient image from view at block 240.

FIG. 4 depicts an exemplary embodiment of a reception interface 249 which includes a summary view 250 of all patients scheduled for the day according to time of appointment 254 (e.g., the 11:45 am time slot is populated by Jonathan Solomon and Thomas Albro). Patients are represented by their image and name. For example, see an exemplary image of Byron Mangum 252 in the summary view 250.

The summary view 250 can be populated by combining schedule information stored in the Practice Management System and/or EHR (FIG. 1 156) with the patient images (for example, 252 and 258) stored in the application database (FIG. 1 146), granularity timeslots depicted are determined by configuration settings in the workflow application (FIG. 3 199). A configuration setting also determines the rate at which the workflow application polls the Practice Management System and/or EHR appointment database(s) (FIG. 1 156), automatically updating the summary view 250. Users can update the summary view at any time by using the Refresh button 274.

When the patient image (for example, image 252 associated with patient Abraham Lincoln's image) is selected with a single-click, the image highlights in the summary view 258 at left and a larger image 268 of the patient displays in a detail area 269 to the right. In this example, the summary view image 258 of Abraham Lincoln is also displayed in the detail area 269 to the right as patient image 268. The detail area 269 includes a heading banner 270 with key patient data, provider data, and appointment data. The detail area 269 also includes patient demographic and insurance information 266 for confirmation and updating by the receptionist. Any change recorded in this detail area 269 will automatically update the Practice Management System and/or EHR (FIG. 1 156) when a "Check In" button 262 is clicked. Immediately when the "Check In" button is clicked, the patient status in the application database is updated, removing the patient image 258, 268 from the summary view 250 and clearing the patient details area, 266, 268, and 270. The patient image then appears automatically on the "Provider" interface for a clinician responsible for the next stage in the patient encounter (see FIG. 11).

When the "Show Checked-In" box 260 is checked by a Reception Interface user 258, the summary view area 250 switches to only show patients already checked-in, allowing the user to review previous activity.

The "Cancellation" button 264 is used by the Receptionist whenever the patient visit is not kept. When clicked, the visit status is changed in the Practice Management System and/or EHR, and the patient image is removed from both the summary view and the patient detail area to the right, 266, 268, and 270.

The vertical space (for example, as occupied by each patient image 252 and 258 occupy time slot 11:30 am, patient image 254 occupies time slot 11:45 am, etc.) allocated to the timeslots in the summary view 250 automatically adjusts according to the number of patient appointments depicted in the timeslot. When no patients are scheduled or remain to be checked-in in a timeslot, that timeslot 272 collapses thereby conserving screen space.

Double-clicking a patient image, for example, patient image 258, automatically displays the chart for that patient in the EHR (also as illustrated in FIG. 10).

Figure 9:
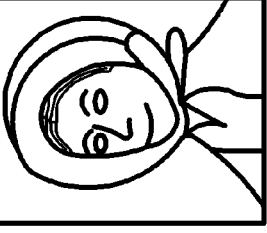
FIG. 9 depicts an exemplary embodiment of an interface for the invention for the purpose of performing a Patient Lookup.

Users needing to find patients whose information is not displayed in the summary view can click the Patient Lookup button 256 to call a patient lookup form (FIG. 9 390) to navigate to the patient information in the Practice Management System and/or EHR. As exemplified in FIG. 9 the patient's image 392 can be associated with patient data such as scheduled appointment date in a calendar 394, provider information 396, patient identification information 398, and the like.

Figure 5:
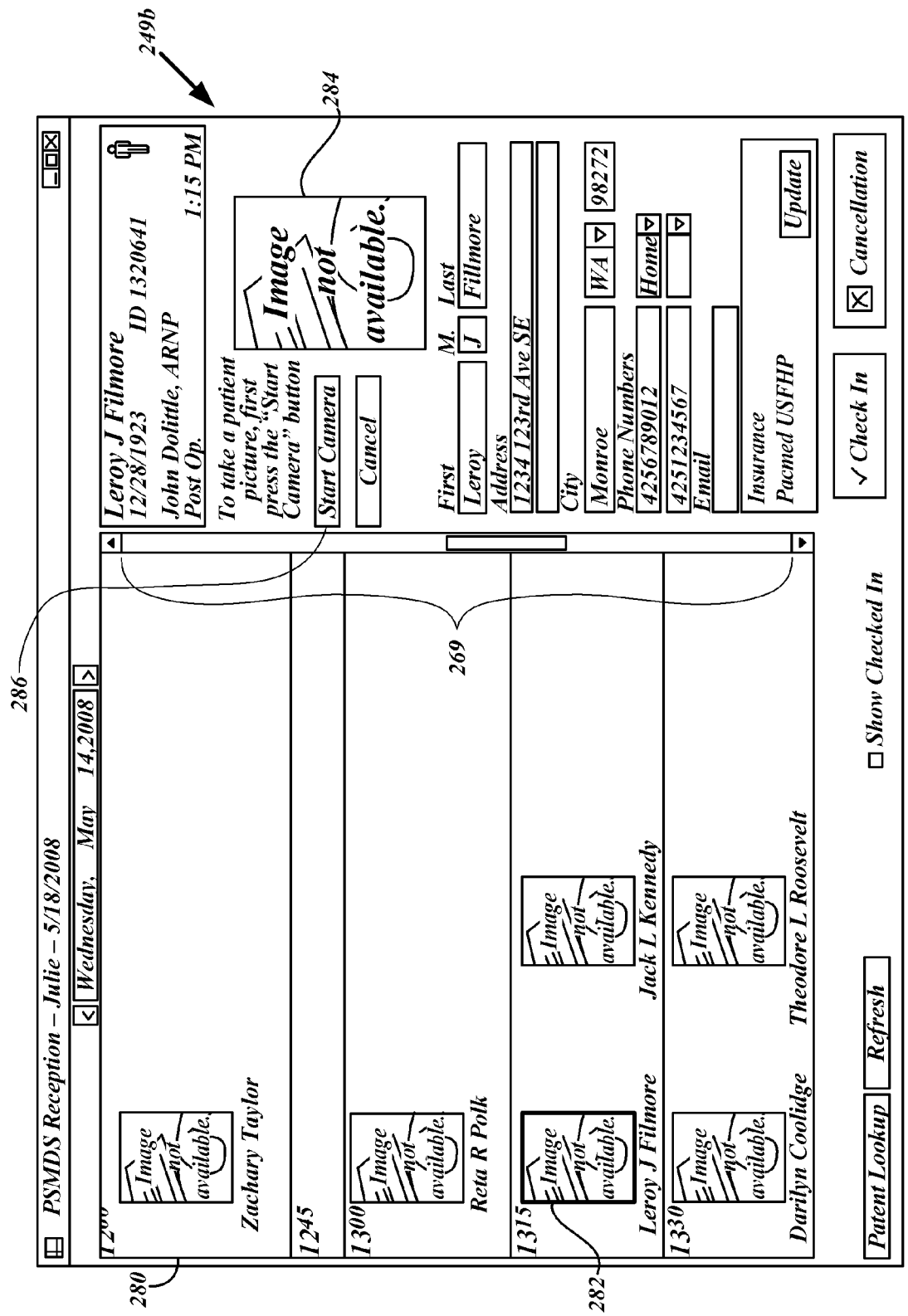
FIG. 5 depicts an exemplary embodiment of the invention and the operation of capturing a patient image.

Turning now to FIG. 5, the summary view 280 of the "Receptionist" interface 249b shows the case where patients images (for example, as previously shown in FIG. 4, 258, 252) are not available due to either recent adoption of the workflow application or patients being new to the clinic. If no image for a patient is stored in the application database (FIG. 1 146), a generic graphic 282 is displayed.

Selecting the generic graphic 282 associated with the patient appointment in the summary view 280, loads the available patient details as previously described (FIG. 4, 266, 268, and 270) except that an enlarged image 284 of the generic graphic 282 is displayed.

Whenever patient information is loaded into the detail view 269, the "Start Camera" button 286 is enabled. When the "Start Camera" button 286 is selected, the generic image 282—changes to show a live video feed (see FIG. 6 288) from a video camera connected to a workstation (FIG. 1, 124). The video feed image area can be larger than the normal patient image making the capture of the image less cumbersome and onerous for the patient. In an exemplary embodiment, the camera can utilize a wide angle lens, accommodating considerable variation in patient height, and also accommodating wheel-chair bound patients. With a larger field, the patient is not required to move to a precise location.

Figure 6:
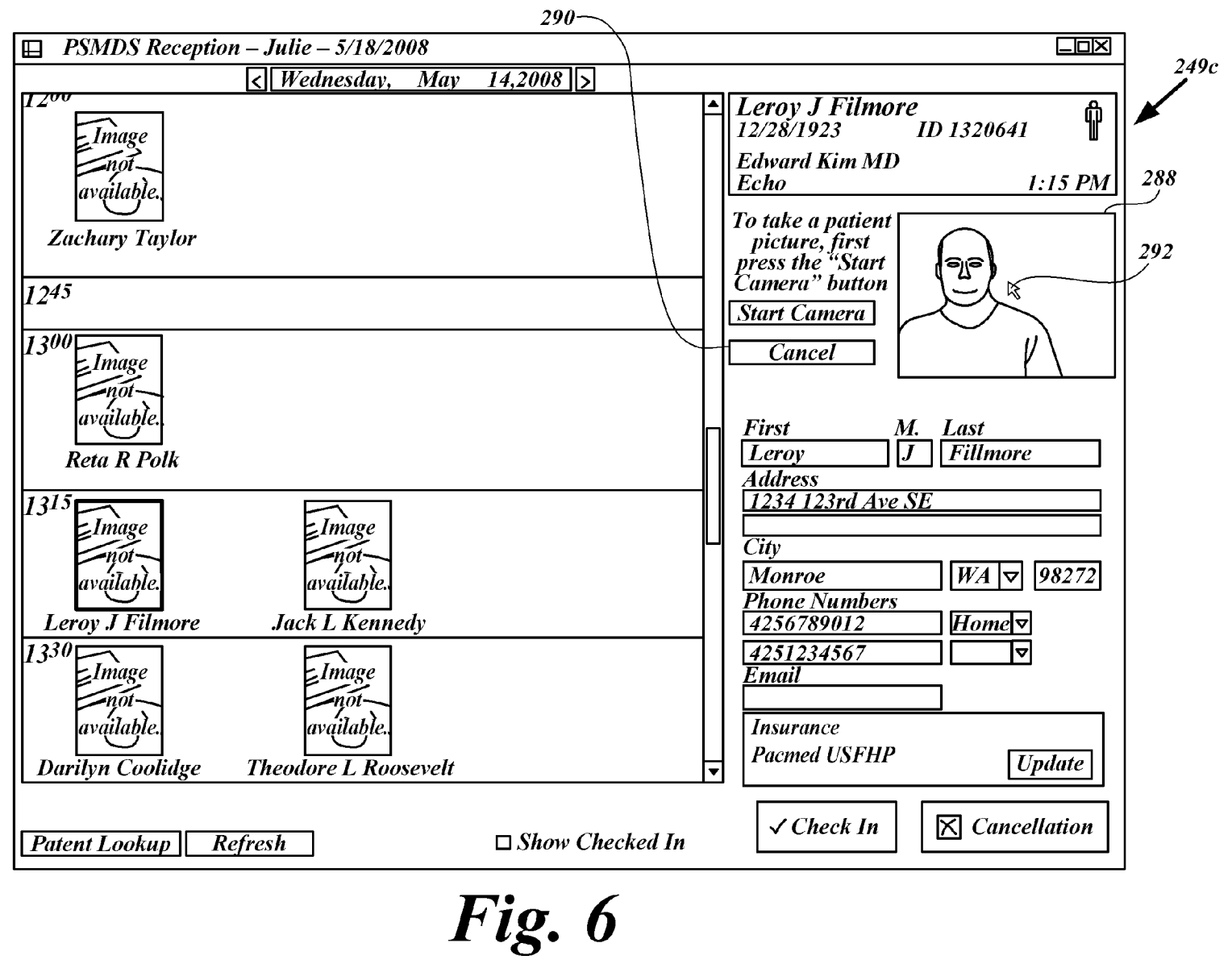
Figure 7:
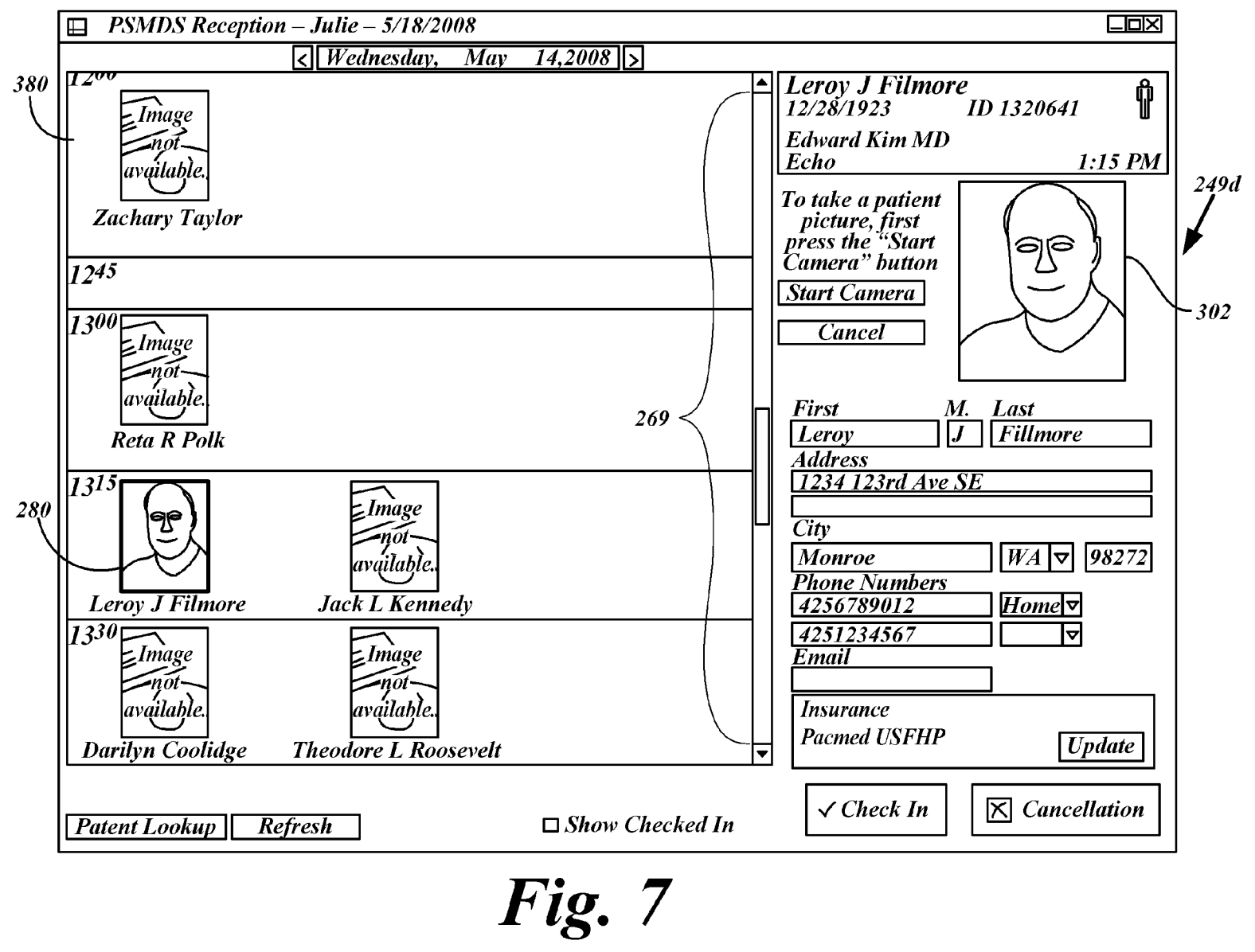

Turning to FIG. 6, in a "Receptionist" interface 249c, an archival patient image 288 is stored when the receptionist clicks within the displayed video stream 292. For example, the point clicked on the patient's nose becomes the center of the archival patient image. The size of the archival patient image is calculated from the center point outward displaying as large a depiction of the patient's face as possible, thereby optimizing the image composition and usefulness (FIG. 7, 302). The image capture process is streamlined for the user, without confirmation prompts or need to focus or direct the video camera. If the image is not centered or not otherwise acceptable, the image can be cancelled by clicking the "Cancel" button 290. The image capture process can be repeated at any time, overwriting the prior image in the workflow application database (FIG. 1 146). Therefore an unsatisfactory or out of date image can be easily and quickly replaced. From start to finish the whole process of image capture and storage takes about a second so as to not negatively impact the receptionist's productivity. At any point during the video stream, the user can select the "Cancel" button 290 and the stored image in the workflow application database (FIG. 1 146) will remain unchanged.

As illustrated in FIG. 7, at a "Receptionist" Interface 249d, once the patient image is clicked and the image processed and stored 300, 302, the display automatically refreshes showing the cropped image in both the summary view 300 and in the patient detail view 302.

FIG. 8 depicts one embodiment of a "Medical Technician (MT)/Medical Assistant (MA)" interface 349 which displays those patients checked-in and assigned to the user in a patient summary view 350, a resource listing 352 (rooms in this case as illustrated in this exemplary embodiment as ECHO1, ECHO2, and so on) showing real-time status, and a list of patient care tasks 364 (e.g., as illustrated under Tab "Results and Requests" in chronological order with patient names and subjects starting at information contained in line 1 362 "Nov. 5, 2007" "Phone" "Taylor Zachary" "Adverse Reaction" and the like).

The patient summary view 350 can be organized by visit type 378 (e.g., patient Grant is associated with Echo Exam Room 3) or by the provider seeing the patient and contains key appointment information, such as appointment time and type 348 and patient name 358 (which in this case is displayed in red to indicate that the patient wait time has exceeded a preset limit).

The resource listing 352 indicates available rooms 354 and occupied rooms 356 with name of patient in the room. The resources shown (e.g. 354, 356) in the resource listing 352 correspond with the major headings 378 in the summary view. For example, in this case the patient image 346 of Dolly Madison 358 selected, the resource listing 352 would immediately update and display available rooms 354 suitable for performing an echocardiogram. In another embodiment, the image (e.g. 346) summary view 350 headings can be provider names. In such a case, selecting a patient will automatically update resource display 352 to show the exams rooms 354, 356 and/or resources 352 most used by the MT provider seeing the patient. This feature allows for a less cluttered interface, minimizes navigation, and speeds the work of the user. This is especially important for drag-and-drop capability. The user can navigate to non-associated or infrequently used resources by using an arrow scrollbar 376 on the right of the resource listing 352.

Tailored resource listings 352 are enabled through a configurable table associating providers and visit types with rooms, equipment, and other resources.

To initiate care and assign a patient to a resource, the patient image 346 (e.g. available room 354 to occupied room 356) is dragged and dropped onto an available resource 354. Doing so updates interfaces resource status in the workflow application database (FIG. 1 146) and updates the display for all system users. Resources with patients assigned to them are displayed in a different format and indicate the name of the patient assigned 356. The application does not allow users to assign patients to unavailable resources (e.g. 356).

Another option allows the user to right-click a resource (e.g. 354) and change its status. For example, in the case of a room it can be denoted as "dirty", "out of service", or any other preconfigured choice.

The patient care tasks 362 are populated automatically if an EHR (FIG. 1 156) is used in conjunction with the workflow application system (FIG. 3 199). Details of a selected task 374 appear in a window below as a patient care task list 372. The patient image 360 is displayed in the detail view and serves as a means of calling the most appropriate form in the EHR for the user to accomplish the task by double-clicking the patient image, e.g. patient Lucy Hayes is highlighted in the selected task list 374 and her image 368 is associated with the Pharmacy Refill task 372 shown in lower right hand panel.

The user can quickly navigate through the pre-determined to associated patient using arrow keys tasks 366 and forward the task to another staff member 368 and 370.

FIG. 11 depicts an embodiment of a provider interface 399 with generally the same organization and behavior as the MA/MT interface 349 previously described in FIG. 8. In this case, the summary view 400 is sorted by patient status, and represented with headings such as Reception 401, Exam Room 402, and Priority 408. Patients in Reception 401, 414 are shown in a different format to indicate they are in the clinic but not yet ready for the provider. Patient listings in the Exam Room 402 area include the time of the appointment, the visit type, the patient name, the patient image (e.g., 404) and room number (e.g., 406).

In this example, patients under the Exam Room 402 heading have completed the MA/MT portion of their encounter and are ready to see the provider. Also in this example, patients listed in the Priority area 408 are not in the clinic but require prompt attention.

The provider task list 409 and associated detail views empower the user to act on the request or information directly in the provider interface 399. In this example, the provider is reviewing transcription 418 relating to patient Frances Cleveland, and can listen to their original dictation using an arrow key 410, edit the text using the "Edit" button 416, and accept the input using the "Accept" button 412 for the permanent record. This aspect of the present invention is fully described in U.S. patent application Ser. No. 12/102,863 filed Apr. 14, 2008 and is herein incorporated by reference.

FIG. 12 depicts an embodiment of a management and administrative interface 449a of the invention which displays the status of all patients, providers, and resources. The management and administrative interface 449a is particularly useful in the administration and management of a clinic in toto; empowering managers and staff with real-time information and enabling better decision making. It also serves as a means for modifying the workflow and adjusting workloads using familiar drag-and-drop actions.

In an exemplary embodiment, at a tabbed interface screen "Clinic Flow" 451, all provider names can be listed in the left most column 450 along with daily patient load 452. The title row 454 indicates patient status in the clinical workflow. Patients who have yet to arrive can be-listed in the "Pending Arrival" column 453, those who are checked-in and in the waiting room can be in the "Reception" column 454, and those with the Medical Assistant can be in the "Medical Assistant" column 455, and those with a provider in an Exam Room can be in "Exam Room" column 457 and those with a provider in a Procedure Room can be in a "Procedure Room" column 459. Images of patients physically in the dine can be prominently displayed, for example patient images 456 and 460 are bold. Images of patients not physically in the clinic ("Pending Arrival," and "Complete"—not shown) are less prominently displayed (e.g., 462, patient Monroe has not yet arrived).

Patient information can includes for example, the patient image (e.g. 456, 458), last name, visit type 456 (e.g., patient Jonathan Solomon is waiting for a consult), projected wait time (e.g., patient Jonathan Solomon has an 18 minute wait), and room location where applicable 458 (e.g., patient Fillmore Stress is in exam room Echo 4). Unique formatting identifies the location of the provider 460.

In one exemplary embodiment projected wait times can be calculated using an algorithm included in the workflow application system (FIG. 3 199). The workflow application server (FIG. 1 147) can maintains-a database of the start and end times for each encounter from which average elapsed times for each visit type can be calculated for each Provider. An anticipated elapsed time can be determined by a moving average over a configurable number of patient visits. The projected wait time for a patient can be derived from an actual start time of the provider's current patient visit, plus the anticipated elapsed time for that visit, plus the anticipated elapsed time for each unseen patient scheduled ahead of the subject patient.

Often the provider's time is the scarcest resource and therefore maximized in the above scenario. This makes the provider most often the determining factor in patient wait times.

The projected wait time for each patient can be recalculated and updated on a configurable polling interval and/or triggered by any patient status changes. Projected wait times can be used to predict move management from a reactive mode to a proactive mode, whereby patient experience can be improved and clinic utilization maximized.

Where long project wait times exist, management can undertake resource and load balancing. Patients in any column (for example, in "Reception" 454), unless currently with a provider (for example, "Medical Assistant" 455, "Exam Room" 457), can be drag-and-dropped from one provider's workflow into another provider's workflow. Doing so automatically updates the Practice Management System and/or the EHR (FIG. 1 156), and also triggers a recalculation of wait times for all patients according to the algorithm as detailed above.

In another embodiment, the Management and Administrative interface 499a depicted in FIG. 12 can display additional information when stretched to take up more screen space. For example, higher resolution patient images can be shown, appointment start times shown, etc., and even font size increased such that when displayed on a large format screen, it functions as a "mission control" display.

Figure 13:
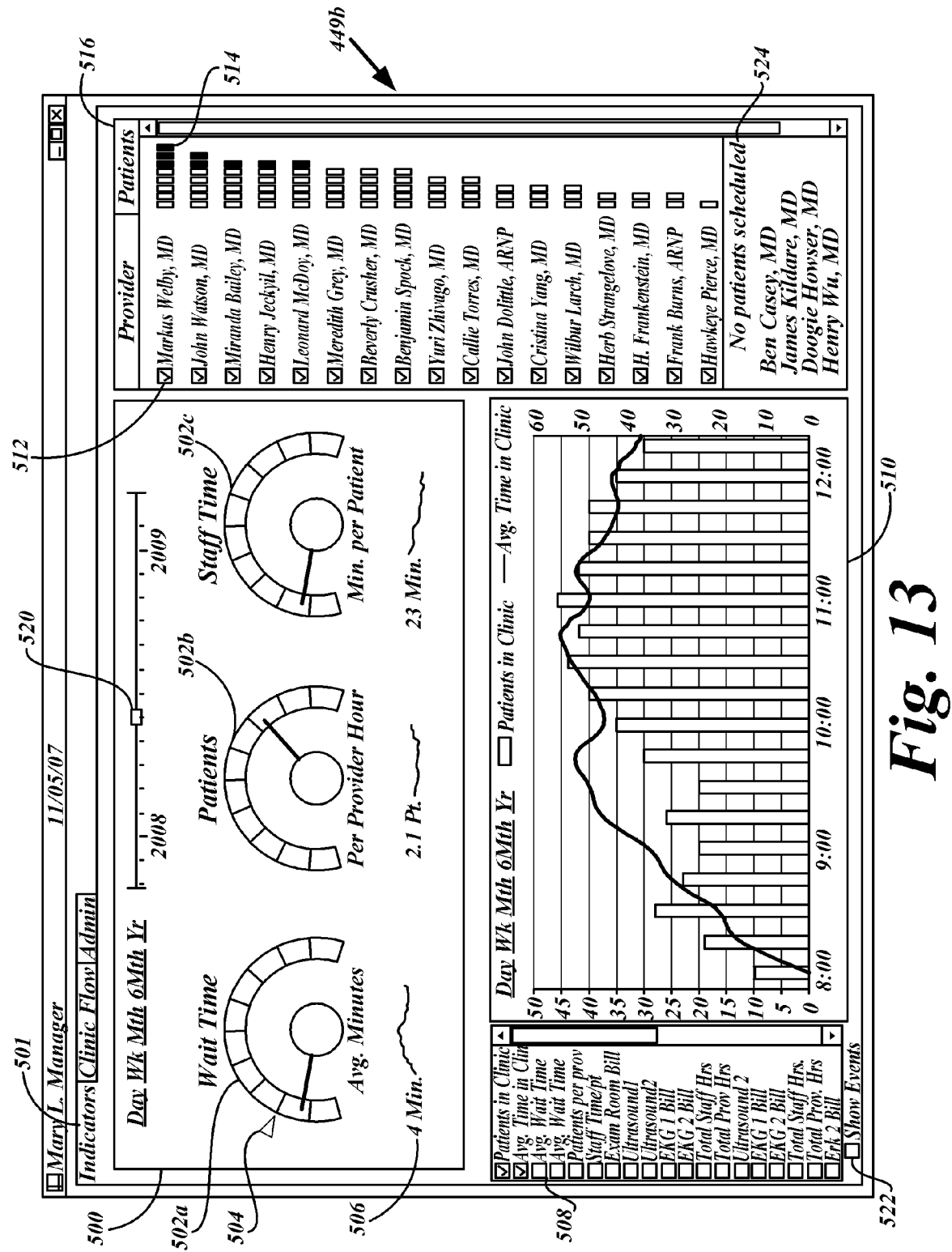
FIG. 13 depicts an exemplary embodiment of an interface for the invention showing clinic performance metrics.

Turning to FIG. 13, an exemplary embodiment of the Management and Administrative interface 449b is illustrated. At a tabbed interface screen "Indicators" 501 can provide managers and staff with real-time information and enable better decision making. In this illustration, key clinic performance indicators can be grouped 500 and illustrated with dial indicators 502a-c in this case for "Patient Wait Time" 502a, "Patients per Provider Hour" 502b, and "Staff Time Per Patient" 502c. A time period can be selected and scrolled backward and forward on the time scale 520. Markers 504 can be preset on the dial indicators 502a-c to reference goals, show past averages or establish warning limits. Alerts can be issued (for example, by email, voice, or other means) when warning limits are exceeded. Trended information 506 can be displayed directly below the dial indicators 502a-c. The key dial indicators 502a-c can include data averaged for the providers selected in the provider list 516, as indicated by a mark in the check box next to each provider's name 512. This allows the key metrics to display information about one provider, a group of providers, and/or the clinic as a whole. The current patient load for each provider can be indicated by hash marks to the right of the provider's name 514. Providers that did not see patients on the current day are listed separately 524 and are not included in the current day's metrics.

Trend graphs 510 can be composed by selecting one or more data elements in the data element list 508. Trend graphs can also be annotated with by clicking a "show events" button 522. Events can include holidays, provider vacations and clinic events. This aspect of the present invention is fully described in U.S. patent application Ser. No. 12/102,863 filed Apr. 14, 2008 and is herein incorporated by reference.

While the particular embodiments of the invention have been illustrated and described, as noted above, many changes can be made without departing from the spirit and scope of the invention. For example, the number of interfaces specific to a particular practice can change, the data fields and the tabbed-category labels can change, the data entry and graphic display can change according to practice specialty, and the interfaces can be modified according to changes in industry standards. Also, the computer systems include at least one computer readable medium or memory for holding instructions programmed according to the teachings of the invention and for containing data structures, tables, records, or other data describe herein. Therefore examples of computer readable media are not constrained by an particular media choice, but include all computer readable media stored on any one or combinations of computer readable media used for controlling the computer systems of the embodiments of the disclosed invention, or for enabling the computer systems disclosed to interact with any human user. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A system for managing patient care workflow and resource allocation in real time in a clinical setting comprising:
an input processor in communication with a workflow management application server and patient record database;
a plurality of workflow management applications on the workflow management application server, each of said workflow management applications associated with at least one of a plurality of system user roles;
a plurality of workflow interfaces associated with the at least one of a plurality of workflow management applications wherein patient information from the patient record database is associated with a patient's health record, the workflow interfaces being configured to:
determine the system user's role;
associate an image of a patient with a first clinic resource by placing and displaying a graphical representation of the image of the patient in a screen portion of the workflow interface associated with the first clinic resource, wherein the workflow management application does not allow users to assign or associate patients to unavailable resources;
track the patient and clinic resource based on the location of the graphical representation of the image;
update the first clinic resource status for all system users;
record when the graphical representation of the image of the patient is associated with a clinic resource;
generate a wait time for a resource;
generate efficiency data based in part on the generated wait time; and
a timing process associated with said input processor configured to generate automatic data updates indicative of patient progress and/or treatment in the clinic.

2. The system for managing patient care workflow and resource allocation of claim 1, wherein a resource allocated to the patient is indicated by associating graphical representations of clinic resources with the image of the patient in the at least one of a plurality of tailored workflow management applications; and adapting a workflow based on the resource being allocated to the patient.

3. The system for managing patient care workflow and resource allocation of claim 1, wherein the image of the patient is associated with the at least one of a plurality of workflow management applications by:
opening the at least one of a plurality of tailored workflow management applications; and
capturing the image of the patient from a streamed video image display generated by a video camera in communication with the workflow management application servers by clicking on the streaming video image.

4. The system for managing patient care workflow and resource allocation of claim 1, wherein the image of the patient-is associated with the at least one of a plurality of tailored workflow management applications and when the image is selected, the images acts as a portal to medical information associated with the patient's health record in the patient record database.

5. The system of managing patient care workflow and resource allocation of claim 1, wherein a plurality of patient images are associated with a screen portion that represents the at least one of a plurality of tailored workflow management applications indicating each patient's real-time status and progress in the at least one of a plurality of tailored workflow applications.

6. The system of claim 1, wherein the user roles of system users associated with the at least one of a plurality of tailored workflow management applications are selected from the group consisting of receptionist, clinical care-provider, medical assistant, clinical assistant, medical technologist, nurse, nurse practitioner, practice manager, medical records manager, clinical practice billing manager, or physician.

7. The system for managing patient care workflow and resource allocation in claim 1, wherein the at least one of a plurality of tailored workflow management applications are specific to a system user's tasks and wherein the tasks are selected from the group consisting of administrative tasks, non-physician care-provider tasks, physician care-provider tasks, technologist tasks, or practice management tasks.

8. A non transitory machine-readable medium encoded with instructions, that when executed by one or more processors, cause the processors to carry out a process for providing a medical management workflow application linked to a patient's health record in response a request of a system user and an assigned role of the system user, the process comprising:
providing at least one of a plurality of workflow management applications, said workflow management applications associated with a plurality of system user roles as determined by a User-Role Database (URD);
providing the at least one of a plurality of workflow management applications associated with a patient's record, wherein the at least one of a plurality of workflow management
applications further comprises:
a user interface configured to:
enable a user of the at least one of the plurality of workflow management applications to track a patient throughout a clinic;
enable a user to activate a resource component based on a graphical representation of an image of a patient being associated with a screen portion of the user interface that is linked to a resource, the resource component configured to:
(1) alert one or more clinical staff members that the patient is ready for the next step of the patient workflow;
(2) update a status for the resource for all system users;
(3) access a patient health record;
(4) calculate efficiency data based in part on a generated wait time; and
(5) modify a patient workflow for the patient; and
a plurality of tasks associated to the system user's role and patient's status in the workflow presented to the system user at a system user specific time in the patient care workflow; and
displaying a link to the patient's health record whereby medical information is recorded and stored in the patient's record, and input from the user automatically updates the medical information in the patient's record.

9. The machine-readable medium of claim 8, wherein a resource allocated to the patient is indicated by associating graphical representations of clinic resources with the image of the patient-in the at least one of a plurality of tailored workflow management applications.

10. The machine-readable medium of claim 8, wherein the process further comprises:
capturing the image of the patient from a streamed video image display generated by a video camera in communication with the workflow management application servers by clicking on the streaming video image; and
associating the image of the patient with the at least one of a plurality of tailored workflow management applications and the patient's health record.

11. The machine-readable medium of claim 8, wherein the image of the patient-is associated with the at least one of a plurality of tailored workflow management applications and is a portal to medical information associated with the patient's health record in the patient record database.

12. The machine-readable medium of claim 8, wherein a plurality of patient images are associated with the at least one of a plurality of tailored workflow management applications indicating each patient's real-time status and progress in the at least one of a plurality of tailored workflow applications.

13. The machine-readable medium of claim 8, wherein the user roles of system users associated with the at least one of a plurality of tailored workflow management applications are selected from the group consisting of receptionist, clinical care-provider, medical assistant, clinical assistant, medical technologist, nurse, nurse practitioner, practice manager, medical records manager, clinical practice billing manager, or physician.

14. The machine-readable medium of claim 8, wherein the at least one of a plurality of tailored workflow management applications are specific to a system user's tasks and wherein the tasks are selected from the group consisting of administrative tasks, non-physician care-provider tasks, physician care-provider tasks, technologist tasks, or practice management tasks.

15. A method in a computing system for managing patient care workflow and resource allocation in real time in a clinical setting comprising:
providing at least one of a plurality of tailored workflow management applications, said tailored workflow management applications associated with a plurality of system user roles as determined by a User-Role Database (URD);
associating the at least one of a plurality of tailored workflow management applications with a patient's health record, wherein the at least one of a plurality of tailored workflow management applications further comprises:
a user interface defining one or more screen portions that are associated with one or more resources, wherein when a graphical representation of the patient is associated with a screen portion associated with one or more resources, the patient is assigned to that resource and an update to the patient status is shown in the user interface for all system users;
the computer system recording when the graphical representation of the image of the patient is associated with a clinic resource;
determining a plurality of tasks associated to the system user's role and patient's status in the workflow and presenting the plurality of tasks to the system user at a system user specific time in the patient care workflow;
the computer system generating a wait time for a resource;
the computer system generating efficiency data based in part on the generated wait time; and
the computer system displaying a link to the patient's health record whereby medical information is recorded and stored in the patient's health record, and input from the user automatically updates the medical information in the patient's health record.

16. The method for managing patient care workflow and resource allocation claim 15, further comprising: dragging the graphical representation of the patient and dropping the representation in a screen portion associated a check in location, such that patient demographic and insurance information is displayed within the user interface.

17. The method for managing patient care workflow and resource allocation of claim 15, wherein the image of the patient is associated with the at least one of a plurality of workflow management applications by:
opening the at least one of a plurality of tailored workflow management applications; and
capturing the image of the patient from a streamed video image display generated by a video camera in communication with the workflow management application servers by clicking on the streaming video image.

18. The method for managing patient care workflow and resource allocation of claim 15, wherein the image of the patient-is associated with the at least one of a plurality of tailored workflow management applications and is a portal to medical information associated with the patient's health record in the patient record database.

19. The method of managing patient care workflow and resource allocation of claim 15, wherein a plurality of patient images are associated with a the at least one of a plurality of tailored workflow management applications indicating each patient's real-time status and progress in the at least one of a plurality of tailored workflow applications.

20. The method of claim 15, wherein the user roles of system users associated with the at least one of a plurality of tailored workflow management applications are selected from the group consisting of receptionist, clinical care-provider, medical assistant, clinical assistant, medical technologist, nurse, nurse practitioner, practice manager, medical records manager, clinical practice billing manager, or physician.

* * * * *